(12) United States Patent
Loginova et al.

(10) Patent No.: US 8,029,773 B2
(45) Date of Patent: Oct. 4, 2011

(54) MASCARA CONTAINING FIBER COMPONENTS

(75) Inventors: Yelena Loginova, Bronx, NY (US); Ralph Macchio, Sparta, NJ (US); Alan Farer, Kinnclon, NJ (US); Toni Kolman, Hillsborough, NJ (US)

(73) Assignee: Coty B.V., Harrlem (NL)

( * ) Notice: Subject to any disclaimer, the term of this patent is extended or adjusted under 35 U.S.C. 154(b) by 1291 days.

(21) Appl. No.: 10/578,772

(22) PCT Filed: Nov. 9, 2004

(86) PCT No.: PCT/EP2004/012855
§ 371 (c)(1),
(2), (4) Date: Jan. 22, 2007

(87) PCT Pub. No.: WO2005/044204
PCT Pub. Date: May 19, 2005

(65) Prior Publication Data
US 2007/0190010 A1    Aug. 16, 2007

(30) Foreign Application Priority Data

Nov. 10, 2003 (DE) .................................. 103 53 486

(51) Int. Cl.
*A61Q 1/10* (2006.01)
(52) U.S. Cl. ...................................................... 424/70.7
(58) Field of Classification Search .................. None
See application file for complete search history.

(56) References Cited

U.S. PATENT DOCUMENTS

| 6,482,400 | B1 | 11/2002 | Collins |
| 6,491,931 | B1 | 12/2002 | Collins |
| 6,503,520 | B1 | 1/2003 | Afriat |
| 2002/0028222 | A1 | 3/2002 | Afriat |
| 2002/0098217 | A1 | 7/2002 | Piot et al. |
| 2002/0110571 | A1 | 8/2002 | Kanji |
| 2002/0142014 | A1 | 10/2002 | Afriat et al. |
| 2002/0192251 | A1 | 12/2002 | Collins |

FOREIGN PATENT DOCUMENTS

| DE | 10033527 A | 1/2002 |
| EP | 1 172 078 A | 1/2002 |
| JP | 57-158714 A | 9/1982 |
| JP | 2001-072533 A | 3/2001 |
| JP | 2001-139825 A | 5/2001 |
| JP | 2001-354546 A | 12/2001 |
| WO | WO 02/49601 A | 6/2002 |

*Primary Examiner* — Jyothsna Venkat
(74) *Attorney, Agent, or Firm* — Millen, White, Zelano, Branigan, P.C.

(57) ABSTRACT

The invention relates to a mascara containing fibre components and a method for producing the same. Said mascara contains (in % by weight) 0.1-10 of at least one oil-soluble or oil-dispersible polymer or copolymer, 0.3-10 of a natural or synthetic fibre with an average length of between 3 and 6 mm, 10-30 of a natural or synthetic wax which hardens at 25° C., 1-10 of a synthetic wax which is liquid at 18° C. and above, 0.5-10 of inorganic pigments, organic colourants and mixtures thereof, 40-80 water and cosmetic auxiliaries, active agents and mixtures thereof making up the remainder up to 100% by weight, wherein said mascara does not contain any water-soluble or water-dispersible hydrophilic polymers, film-forming agents, thickeners or clays. The fibres are separated very well and the mascara shows a very good balance between its adhesive properties and the brittleness of the mascara film.

12 Claims, No Drawings

MASCARA CONTAINING FIBER COMPONENTS

The invention relates to a mascara containing fibre components.

It is already known to incorporate fibres in mascara compositions. The main advantage of mascara containing fibres is an elongation of the eyelashes and a certain volume effect. The drawback of such a mascara is its bad usage characteristics during the normal daily time of use (as a rule 8 to 12 hours/day). There are three properties which are usually considered in respect of the usage characteristics of a fibre mascara, which have shown in practice:

1) Detachment of the fibres from the eyelashes, which indicates insufficient adhesive properties of the film-forming agents selected;
2) Flaking, which indicates an imbalance between the adhesive properties and the brittleness of the film formed on the eyelashes;
3) A drying time which is too short or too long. If it is too long, rapid successive application processes can result in that fibres will detach from the eyelashes. If the drying time is too short, the mascara cannot be applied without lumps and each attempt to separate the eyelashes from one another can result in that the fibres will detach from the eyelashes.

Each of the aforesaid properties alone or combined with one another minimizes the beauty characteristics of the mascara concerned, as well as its safety if fragments thereof fall into the eyes and the eyes are rubbed in order to remove the strange objects. All disadvantages of detached fibres make this product undesirable for the consumer.

According to the formula specified, all known formulations of fibre mascara use water-soluble or water-dispersible polymers/film-forming agents alone or in combination with oil-soluble or oil-dispersible film-forming agents/polymers (U.S. Pat. No. 6,491,931; US application 2002/0,110,571; US application 2002/0,192,251; U.S. Pat. No. 6,482,400).

The majority of water-soluble film-forming agents are most effective in the pH range between 4 and 6. In general, the pH range of mascara is between 7 and 8, whereby the characteristics of the film-forming polymer are modified. Also, most of these polymers/film-forming agents are hygroscopic and require the presence of special agents in order to reduce their hygroscopic properties and improve wear.

The production process includes a step in the preparation of the mixture which is of special importance for a mascara containing fibres—the control and maintenance of fibre dispersion, which ensures the uniform quality of the product's performance characteristics. The method described in US 2002/0,110,571 relates to that the fibre dispersion is added into the aqueous phase at between 85 and 90° C., following thickeners, pigments and the other ingredients of the aqueous phase.

The object of the present invention is to provide a mascara containing fibre components, wherein the fibres are separated very well and the mascara shows a very good balance between its adhesive properties and the brittleness of the mascara film.

Another object is to provide a method for producing the aforesaid mascara.

The mascara of the present invention comprises
0.1 to 10% by weight of at least one oil-soluble or oil-dispersible polymer or copolymer,
0.3 to 10% by weight of a natural or synthetic fibre with an average length of between 3 and 6 mm,
10 to 30% by weight of a natural or synthetic wax which hardens at 25° C.,
1 to 10% by weight of a synthetic wax which is liquid at 18° C. and above,
0.5 to 10% by weight of inorganic pigments, organic colourants and mixtures thereof,
40 to 80% by weight water
and cosmetic auxiliaries, active agents and mixtures thereof making up the remainder up to 100% by weight,
wherein said mascara does not contain any water-soluble or water-dispersible hydrophilic polymers, film-forming agents, thickeners or clays,
and wherein all percentages are relative to the weight of the overall composition.

The invention results in a fibre mascara composition which contains only hydrophobic film-forming agent(s) and has a very good ability to retain the fibres. The method for producing the aforedescribed mascara includes an intermediate step in which the fibres are premixed with the polymer in the cold state, and the premix obtained in this way is subsequently added into the emulsion.

It is preferred that the fibres contained in the mascara have an average length of between 4 and 4.5 mm.

Said fibres can be selected from among polyester fibres, rayon fibres, nylon fibres, cotton fibres, Teflon fibres, and are preferably Lycra® fibres.

The oil-soluble or oil-dispersible polymer is selected from the group consisting of copolymers of maleic anhydride, isopropylmaleate and olefin monomers having between 30 and 45 carbon atoms; copolymers of vinylpyrrolidone and long-chain alpha-olefins; copolymers of adipic acid with fumaric acid, phthalic acid and tricyclodecane dimethiconol; copolymers of adipic acid, cyclohexanedimethanol, maleic anhydride, neopentyl glycol and trimellitic anhydride monomers; co-polymers of adipic acid and PPG-10 monomers; polyethylene; butadiene/isoprene copolymers; copolymers of ethyl esters or butyl esters of PVM/MA copolymers; Tricontanyl PVP; C20-40 Acid (and) Polyethylene; PVP/Eicosene; Bis-Diglyceryl Polyacyladipate-1; Polyvinyl Octadecyl Ether; and mixtures thereof; or another oil-soluble or oil-dispersible polymer, film-forming agent or oil-thickening/oil-gelatinizing agent.

Tricontanyl PVP, C20-40 Acid (and) Polyethylene and PVP/Eicosene (PVP=polyvinylpyrrolidone) are particularly preferred. The oil-soluble or oil-dispersible polymer is preferably used in an amount ranging between 0.5 and 7% by weight.

Auxiliaries are fragrances, markers, vitamins, antioxidants and protective agents which are effective against Gram-positive and Gram-negative bacteria, yeasts and forming agents. Further gelatinizing agents/thickeners for the oil phase are, in addition to the aforesaid oil-soluble or oil-dispersible polymers, such products as C20-40 Acid (and) Polyethylene, Decene/Butene Copolymer, Disteardimonium Hectorite.

Surface-active agents for the W/O emulsion are e.g. Lecithin, Sorbitan Sesquioleate or any other having a low HLB.

Preferred surface-active agents for O/W emulsions are e.g. Polysorbate 20, Oleth-20 or any other having a high HLB.

Inorganic pigments are e.g. iron oxides, titanium dioxide, ultramarine, mica, chromium oxide, chromium hydroxide. Organic colourants can also be used, such as FD&C Red 40, FD&C Yellow 5, FD&C Blue 1 and their lacquers as well as Green D&C 5, with Carmine.

The mascara of the present invention has good characteristics as regards improved application, elongation, volume increase and curling of the eyelashes. The composition can be applied to the eyelashes alone, or it can be covered with a layer of another mascara based on a regular emulsion of the "waterproof" or "gel" category, i.e. as sublayer or top layer mascara. The composition can also be used as a filler for the eyebrows. The composition has a unique lump-free fibre retention power.

Natural or synthetic waxes hardening at 25° C. are e.g. beeswax, ozokerite, carnauba wax, candelilla wax, wool wax, hard paraffin, ceresin, silicone wax, polyethylene glycol waxes or polyethylene glycol ester waxes.

A preferred wax which liquefies at 18° C. and above is e.g. a polyethylene wax, a synthetic wax (INCI: Synthetic Wax) or VP/Hexadecene Copolymer with this characteristic.

The method for producing the fibre mascara, as described in the present invention, envisages a controllable separation of the preparation of the fibre dispersion in a clear basic formulation (liquid synthetic wax). The inventive process for producing the mascara comprises: mixing of an oil phase containing waxes, oils, pigments and at least one oil-soluble or oil-dispersible polymer or copolymer with an aqueous phase at between 65 and 78° C. until complete emulsification, and, subsequently, mixing of the homogeneous mixture of fibres and liquid synthetic wax, liquid polyethylene or another liquid polymeric film-forming agent while stirring and at between 50 and 70° C. with the emulsion with which the fibre mixture has been prepared. Said fibre emulsion is prepared by stirring at between 12 and 20 rpm and 18 to 25° C.

The fibre emulsion/dispersion is prepared without adding alcohol.

It is also advantageous that no water-soluble or water-dispersible polymers, film-forming agents, thickeners or clays are contained.

The present method, which is carried out at room temperature (18 to 25° C.) and with very low stirring powers over a period of time of between 5 and 15 min, yields a very stable fibre dispersion with an excellent fibre distribution.

The adhesion of the inventive mascara was compared with that of market products in comparative tests. In these tests, it was found that adhesion was improved by 15-20%, and consumer tests showed excellent judgements as regards fibre distribution and application of the mascara.

The overall emulsion has a pH value of 7-8 and is thus tolerated very well by the user.

The invention will now be explained in detail by means of examples. All quantities are in percent by weight unless indicated otherwise.

EXAMPLE 1

Mascara I

| PHASE A | |
|---|---|
| Carnauba Wax | 4 |
| Ozokerite | 2 |
| Paraffin | 4 |
| Stearic Acid | 4 |
| Sorbitan Sesquioleate | 1 |
| Beeswax | 6 |
| Tricontanyl PVP | 2 |
| PHASE B | |
| Pigment Black Oxide | 8 |
| PHASE C | |
| Simethicone | 0.2 |
| PHASE D | |
| Water | q.s. ad 100 |
| Triethanolamine | 1.5 |
| Propylene Glycol | 1.8 |
| PHASE E | |
| Synthetic wax (liquid at 20° C.) | 5 |
| Rayon fibre | 1 |
| PHASE F | |
| Vitamin | 1.2 |
| PHASE G | |
| Preservative | 1.0 |

The oil phase (A) is heated up to between 80 and 85° C. The pigments of Phase (B) are added and homogenized for 20 min at 2500 rpm. Then, Simeticone (C) is added. The water phase (D) is heated up to 75° C. and mixed at between 200 and 300 rpm. Both phases are combined with one another and homogenized for 20 min at 2500 rpm. In doing so, the temperature is maintained at between 65 and 70° C. Subsequently, the mixture is cooled down to between 60 and 55° C.

The fibres are premixed with the synthetic wax of Phase (E) at 20° C. and between 15 and 20 rpm for 5 to 10 min. The mixture is filled into the main container at between 60 and 65° C. Subsequently, Phases F and G are added at a lower temperature.

The important step of this method is the treatment of the fibres with the liquid synthetic wax in order to order and separate the fibres, thus obtaining a lump-free fibre dispersion. This is a "cold" process which takes place as an intermediate step before the fibres are incorporated into the emulsion. The aforedescribed treatment enables a good fibre dispersion to be maintained. The fibre phase is added into the other mixture using a stirrer with moderate stirring behaviour at 65° C.

EXAMPLE 2

Mascara II

| PHASE A: | |
|---|---|
| Beeswax | 5 |
| Montan Wax | 3 |
| Candelilla Wax | 2 |
| Stearic Acid | 5 |
| Lecithin | 1 |
| Microcrystalline wax | 4 |
| C20-40 Acid (and) Polyethylene | 3 |
| PHASE B: | |
| Pigment Black Oxide | 9 |
| PHASE C: | |
| Water | q.s. ad 100 |
| Triethanolamine | 1.7 |
| Glycerine | 1 |
| PHASE D: | |
| VP/Hexadecene Copolymer | 6 |
| Rayon fibre | 2 |
| Polyurethane - "Lycra" fibre | 1 |
| PHASE F: | |
| Vitamin | 1 |

| PHASE G: | |
|---|---|
| Preservative | 0.8 |

The oil phase was prepared, as well as the aqueous phase. Both phases were combined with one another as described above. Then, the fibres were premixed with VP/Hexadecene Co-polymer and said premix was added into the main emulsion as explained in Example 1.

The invention claimed is:

1. A method for producing a mascara containing a fiber component comprising
   (a) mixing an oil phase comprising waxes, oil, pigment and at least one oil-soluble or oil-dispersible polymer or copolymer with an aqueous phase at 65-78° C. until complete emulsification is achieved, and
   (b) mixing the emulsion of step (a) at 50-70° C. by stirring with a homogeneous, alcohol-free mixture of fiber and liquid synthetic wax, liquid polyethylene or mixtures thereof, which has been prepared at between 18 and 25° C.

2. The method according to claim 1, wherein said at least one oil-soluble or oil-dispersible polymer or copolymer is a copolymer of maleic anhydride, an isopropylmaleate and olefin monomer having between 30 and 45 carbon atoms; a copolymer of vinylpyrrolidone and long-chain alpha-olefins; a copolymer of adipic acid with fumaric acid, phthalic acid and tricyclodecane dimethiconol; a copolymer of adipic acid, cyclohexanedimethanol, maleic anhydride, neopentyl glycol and trimellitic anhydride monomer; a copolymer of adipic acid and a PPG-10 monomer; polyethylene; butadiene/isoprene copolymers; copolymers of ethyl esters or butyl esters of PVM/MA copolymers; Tricontanyl PVP; C20-40 Acid (and) Polyethylene; PVP/Eicosene; Bis-Diglyceryl Polyacyladipate-1; Polyvinyl Octadecyl Ether; or a mixture thereof.

3. The method according to claim 2, wherein said at least one oil-soluble or oil-dispersible polymer or copolymer is Tricontanyl PVP, C20-40 Acid (and) Polyethylene, PVP/Eicosene or a mixture thereof.

4. The method according to claim 1, wherein said fiber is poly-ester, rayon, nylon, cotton, Teflon or spandex.

5. The method according to claim 1, wherein the fiber has an average length of between 4 and 4.5 mm.

6. The method according to claim 1, wherein said oil phase wax is a natural or synthetic wax which is solid at 25° C. and below.

7. The method according to claim 4, wherein said fiber is spandex.

8. The method according to claim 6, wherein said oil phase wax is beeswax, ozokerite, carnauba wax, candelilla wax, wool wax, hard paraffin, ceresin, silicone wax, a polyethylene glycol wax or a polyethylene glycol glycol ester wax.

9. A method according to claim 1 wherein said oil phase comprises 0.5 to 7% by weight of at least one oil-soluble or oil-dispersible polymer or copolymer and 0.5 to 10% by weight of an inorganic pigment.

10. A method according to claim 1, wherein said emulsion of step (a) is mixed with 0.3 to 10% by weight of a natural or synthetic fiber and 1 to 10% by weight of a liquid synthetic wax.

11. The method of claim 1, wherein no water-soluble or water-dispersible hydrophilic polymers, film-forming agents, thickeners or clays are added to the mascara.

12. A method according to claim 1, wherein the homogeneous, alcohol-free mixture of fiber and liquid synthetic wax, liquid polyethylene or a mixture thereof, has been prepared at between 18 and 25° C. and stirring at 12-20 rpm before incorporation into the emulsion of step (a).

* * * * *